(12) United States Patent
Francisco et al.

(10) Patent No.: US 11,180,491 B2
(45) Date of Patent: *Nov. 23, 2021

(54) METHOD OF TREATING COVID-19 BY ADMINISTERING THE CCR5/CCL5 (RANTES) INTERACTION INHIBITOR MARAVIROC

(71) Applicant: IncellDx, Inc., San Carlos, CA (US)

(72) Inventors: Edgar B. Francisco, San Carlos, CA (US); Hallison Rodrigues, San Carlos, CA (US); Amruta Pise, San Carlos, CA (US); Bruce K. Patterson, Menlo Park, CA (US)

(73) Assignee: IncellDx, Inc., San Carlos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/067,191

(22) Filed: Oct. 9, 2020

(65) Prior Publication Data

US 2021/0032355 A1 Feb. 4, 2021

Related U.S. Application Data

(62) Division of application No. 16/932,636, filed on Jul. 17, 2020.

(60) Provisional application No. 63/033,445, filed on Jun. 2, 2020, provisional application No. 63/016,155, filed on Apr. 27, 2020.

(51) Int. Cl.
| | |
|---|---|
| *C07D 451/00* | (2006.01) |
| *A61P 31/14* | (2006.01) |
| *C07K 14/52* | (2006.01) |
| *C07K 14/47* | (2006.01) |
| *C07K 16/28* | (2006.01) |
| *A61K 39/00* | (2006.01) |
| *A61K 31/46* | (2006.01) |

(52) U.S. Cl.
CPC ............ *C07D 451/00* (2013.01); *A61P 31/14* (2018.01); *C07K 14/4722* (2013.01); *C07K 14/523* (2013.01); *A61K 31/46* (2013.01); *A61K 2039/505* (2013.01); *C07K 16/2866* (2013.01); *C07K 2317/21* (2013.01); *C07K 2317/24* (2013.01); *C12N 2770/20011* (2013.01)

(58) Field of Classification Search
CPC .............. C07K 14/523; C07K 14/4722; C07D 451/00; A61P 31/14; C12N 2770/20011
See application file for complete search history.

(56) References Cited

U.S. PATENT DOCUMENTS

| | | |
|---|---|---|
| 11,045,546 B1 | 6/2021 | Kelly et al. |
| 2005/0220790 A1 | 10/2005 | Proost et al. |
| 2006/0165650 A1 | 7/2006 | Pavone et al. |
| 2009/0148455 A1 | 6/2009 | Fischer et al. |
| 2012/0077733 A1 | 3/2012 | Weber et al. |
| 2012/0201826 A1 | 8/2012 | Fischer et al. |
| 2013/0303512 A1 | 11/2013 | Pestell |
| 2014/0109245 A1 | 4/2014 | Pestell |
| 2014/0377278 A1 | 12/2014 | Elinav et al. |
| 2015/0079099 A1 | 3/2015 | Fischer et al. |
| 2017/0231991 A1 | 8/2017 | Pestell |
| 2018/0303830 A1 | 10/2018 | Pestell et al. |

OTHER PUBLICATIONS

Adedeji, A. O., et al., May 2013, Novel inhibitors of severe acute respiratory syndrome coronavirus entry that act by three distinct mechanisms, J. Virol. 87(14):8017-8028.*
Kandeel, M., et al., 2020, Small molecule inhibitors of Middle East respiratory syndrome coronavirus fusion by targeting cavities on heptad repeat trimers, Biomol. Ther. 28(4):311-319 (published electronically Mar. 4, 2020).*
Liu, T., et al., Jan. 2013, Design, synthesis and biological evaluation of novel piperazine derivatives as CCR5 antagonists, PLoS ONE 8(1):e53636, pp. 1-7.*
Wang, M.-Y., et al., Nov. 2020, SARS-CoV-2: Structure, biology, and structure-based therapeutics development, Front. Cell. Infect. Microbiol. 10:Article 587269, pp. 1-17.*
Iannaccone, G., et al., Jun. 2020, Weathering the cytokine storm in COVID-19: Therapeutic implications, Cardiorenal Med. 10:277-287.*
Okamoto, M., et al., Jul. 2020, The chemokine receptor antagonist cenicriviroc inhibits the replication of SARS-CoV-2 in vitro, Antivir. Res. 182:104902, pp. 1-6.*
Akalin, E., et al., Apr. 24, 2020, Covid-19 and kidney transplantation, New Engl. J. Med. 382:2475-2477.*
Clinical Trial NCT04343651, Apr. 13, 2020, first posting, Study to evaluate the efficacy and safety of leronlimab for mild to moderate COVID-19, pp. 1-9.*
Baba, M., et al., Nov. 2005, TAK-652 inhibits CCR5-mediated human immunodeficiency virus type 1 infection in vitro and has favorable pharmacokinetics in humans, Antimicrob. Agents Chemother. 49(11):4584-4591.*
Kim, M. B., et al., 2016, CCR5 receptor antagonists in preclinical to phase II clinical development for treatment of HIV, Expert Opinion on Investigational Drugs, 25(12):1377-1392.*
Pulley, S. R., 2007, CCR5 antagonists: from discovery to clinical efficacy, in Chemokine Biology-Basic Research and Clinical Application, vol. II, Neote, K., et al., eds., pp. 145-163.*
Schall, T. J., and A. E. I. Proudfoot, May 2011, Overcoming hurdles in developing successful drugs targeting chemokine receptors, Nat. Rev. Immunol. 11:355-363.*
Adedeji et al., Novel Inhibitors of Severe Acute Respiratory Syndrome Coronavirus Entry That Act by Three Distinct Mechanisms, Journal of Virology, Jul. 2013, vol. 87, No. 14, p. 8017-8028.

(Continued)

*Primary Examiner* — Jeffrey S Parkin
(74) *Attorney, Agent, or Firm* — Bret E. Field; Bozicevic, Field & Francis LLP

(57) ABSTRACT

Methods of treating a subject suffering from COVID-19 are provided. Aspects of the methods including administering to the subject an effective amount of an inhibitor of CCR5/CCL5 interaction, such as a CCR5 antagonist. Also provided are methods of assessing severity of a disease involving hypercytokinemia, such as COVID-19, by determining the level of CCL5/RANTES in a subject, as well as compositions for use in such methods.

3 Claims, 4 Drawing Sheets

(56) References Cited

OTHER PUBLICATIONS

Basu et al., Novel Small Molecule Entry Inhibitors of Ebola Virus, The Journal of Infectious Diseases, Oct. 2015, vol. 212, Suppl. 2, p. S425-S434.

Carrol et al., The Role of RANTES in Meningococcal Disease, The Journal of Infectious Diseases, Jul. 2000, vol. 182, No. 1, p. 363-366.

John et al., Low Levels of RANTES are Associated with Mortality in Children with Cerebral Malaria, The Journal of Infectious Diseases, Sep. 2006, vol. 194, No. 6, p. 837-845.

Kandeel et al., Small Molecule Inhibitors of Middle East Respiratory Syndrome Coronavirus Fusion by Targeting Cavities on Heptad Repeat Trimers, Biomolecules & Therapeutics, Mar. 2020, vol. 28, No. 4, p. 311-319.

Papa et al., Cytokines as Biomarkers of Crimean-Congo Hemorrhagic Fever, Journal of Medical Virology, Jan. 2016, vol. 88, No. 1, p. 21-27.

Reddy et al., Correlation of Plasma Viral Loads and Presence of Chikungunya IgM Antibodies with Cytokine/Chemokine Levels During Acute Chikungunya Virus Infection, Journal of Medical Virology, Aug. 2014, vol. 86, No. 8, p. 1393-1401.

Reynolds et al., Ebola and Marburg Virus Vaccines, Virus Genes, Apr. 2017, vol. 53, p. 501-515.

Sun et al., Host Cytokine Storm is Associated With Disease Severity of Severe Fever With Thrombocytopenia Syndrome, The Journal of Infectious Diseases, Oct. 2012, vol. 206, No. 7, p. 1085-1094.

Olson et al. CurrOpin HIV AIDS, Mar. 2009;4(2):104-111.

Cytodyn, Inc., Leronlimab Under Evaluation for Potential Treatment of Coronavirus: CytoDyn and IncellDX in discussions with potential partners about the use of leronlimab to treat 2019 Novel Coronavirus (2019-nCoV), Jan. 28, 2020, 4 pages.

Huang et al., An Interferon-gamma-Related Cytokine Storm in SARS Patients, Journal of Medical Virology, Feb. 2005, vol. 75, No. 2, p. 185-194.

Ruiz-Mateos et al., Virological Response after Short-Term CCR5 Antagonist Exposure in HIV-Infected Patients: Frequency of Subjects with Virological Response and Associated Factors, Antimicrobial Agents and Chemotherapy, Oct. 2011, vol. 55, No. 10, p. 4664-4669.

Akalin et al., Covid-19 and Kidney Transplantation, The New England Journal of Medicine, URL=https://www.nejm.org/doi/full/10.1056/NEJMc2011117, Apr. 24, 2020, and including the Supplement to: Akalin E, Azzi Y, Bartash R, et al. Covid-19 and kidney transplantation. N Engl J Med 2020;382:2475-7. DOI: 10.1056/NEJMc2011117 (11 total pages).†

U.S. National Library of Medicine, Study to Evaluate the Efficacy and Safety of Leronlimab for Mild to Moderate COVID-19, URL=https://clinicaltrials.gov/ct2/show/NCT04343651, first posted Apr. 13, 2020, downloaded May 21, 2020. (9 pages).†

* cited by examiner
† cited by third party

METHOD OF TREATING COVID-19 BY ADMINISTERING THE CCR5/CCL5 (RANTES) INTERACTION INHIBITOR MARAVIROC

CROSS-REFERENCE TO RELATED APPLICATIONS

This application is a division of U.S. patent application Ser. No. 16/932,636 filed Jul. 17, 2020, which application, pursuant to 35 U.S.C. § 119 (e), claims priority to the filing dates of U.S. Provisional Patent Application Ser. No. 63/016,155 filed Apr. 27, 2020 and 63/033,445 filed Jun. 2, 2020, the disclosures of which applications are herein incorporated by reference.

INTRODUCTION

Severe acute respiratory syndrome coronavirus 2 (SARS-CoV-2), the causative agent of coronavirus disease 2019 was first reported in December 2019. Since the initial cases of COVID-19 were reported from Wuhan, China in December 2019 (Huang, C. et al. Clinical features of patients infected with 2019 novel coronavirus in Wuhan, China. Lancet 395, 497-506 (2020)), SARS-CoV-2 has emerged as a global pandemic with an ever-increasing number of severe cases requiring invasive external ventilation that threatens to overwhelm health care systems (World Health Organization. Coronavirus disease (COVID-2019) situation reports. See website made up of "https://www." before "who.int/emergencies/disease/novel-coronavirus-2019/situation-reports"). While it remains unclear why COVID-19 patients experience a spectrum of clinical outcomes ranging from asymptomatic to severe disease, the salient features of COVID-19 pathogenesis and mortality are rampant inflammation and CRS leading to ARDS (Mehta, P. et al. COVID-19: consider cytokine storm syndromes and immunosuppression. Lancet 395, 1033-1034 (2020); Qin, C. et al. Dysregulation of immune response in patients with COVID-19 in Wuhan, China. Clin. Infect. Dis. (2020)). Indeed, excessive immune cell infiltration into the lung, cytokine storm, and ARDS have previously been described as defining features of severe disease in humans infected with the closely related betacoronaviruses SARS-CoV and MERS-CoV (Channappanavar, R. & Perlman, S. Pathogenic human coronavirus infections: causes and consequences of cytokine storm and immunopathology. Semin Immunopathol 39, 529-539 (2017); Nicholls, J. M. et al. Lung pathology of fatal severe acute respiratory syndrome. Lancet 361, 1773-1778 (2003)).

The C-C chemokine receptor 5 (CCR5) was discovered to be one of the major HIV-1 co-receptors. Therefore, CCR5 blockade using small molecule inhibitors or humanized monoclonal antibodies has been therapeutically deployed to protect certain critical immune cells populations, such as memory CD4 T-cells and monocytes/macrophages that express CCR5, from being infected. Since CCR5 and its ligand CCL5 (RANTES) are also important in a host of other diverse diseases, such as non-alcoholic steatohepatitis (NASH), graft versus host disease (GvHD), and cancer, the effects of CCR5 blockade have been extensively investigated.

In cancer, CCL5 is produced by both tumor cells but more importantly in CD3+ lymphocytes in the tumor microenvironment (TME) which are brought in by CXCL9 and CXCL10 which are produced by CD68+ myeloid cells. CCL5 causes further migration of macrophages and other immune cells into the TME where they produce anti-tumor pro-inflammatory cytokines. CCR5 blockade breaks this cycle by repolarizing macrophages from a pro-tumor M2 phenotype to an anti-tumor M1 phenotype. In addition, CCR5 blockade blocks the influx of regulatory T-cells that express CCR5 and inhibit both the innate and cell-mediated immune responses that function both in cancer immunology and viral infections.

SUMMARY

Methods of treating a subject suffering from COVID-19 are provided. Aspects of the methods including administering to the subject an effective amount of an inhibitor of CCR5/CCL5 interaction, such as a CCR5 antagonist. Also provided are methods of assessing severity of a disease involving hypercytokinemia, such as COVID-19, by determining the level of CCL5/RANTES in a subject, as well as compositions for use in such methods.

DEFINITIONS

Figure 1A:
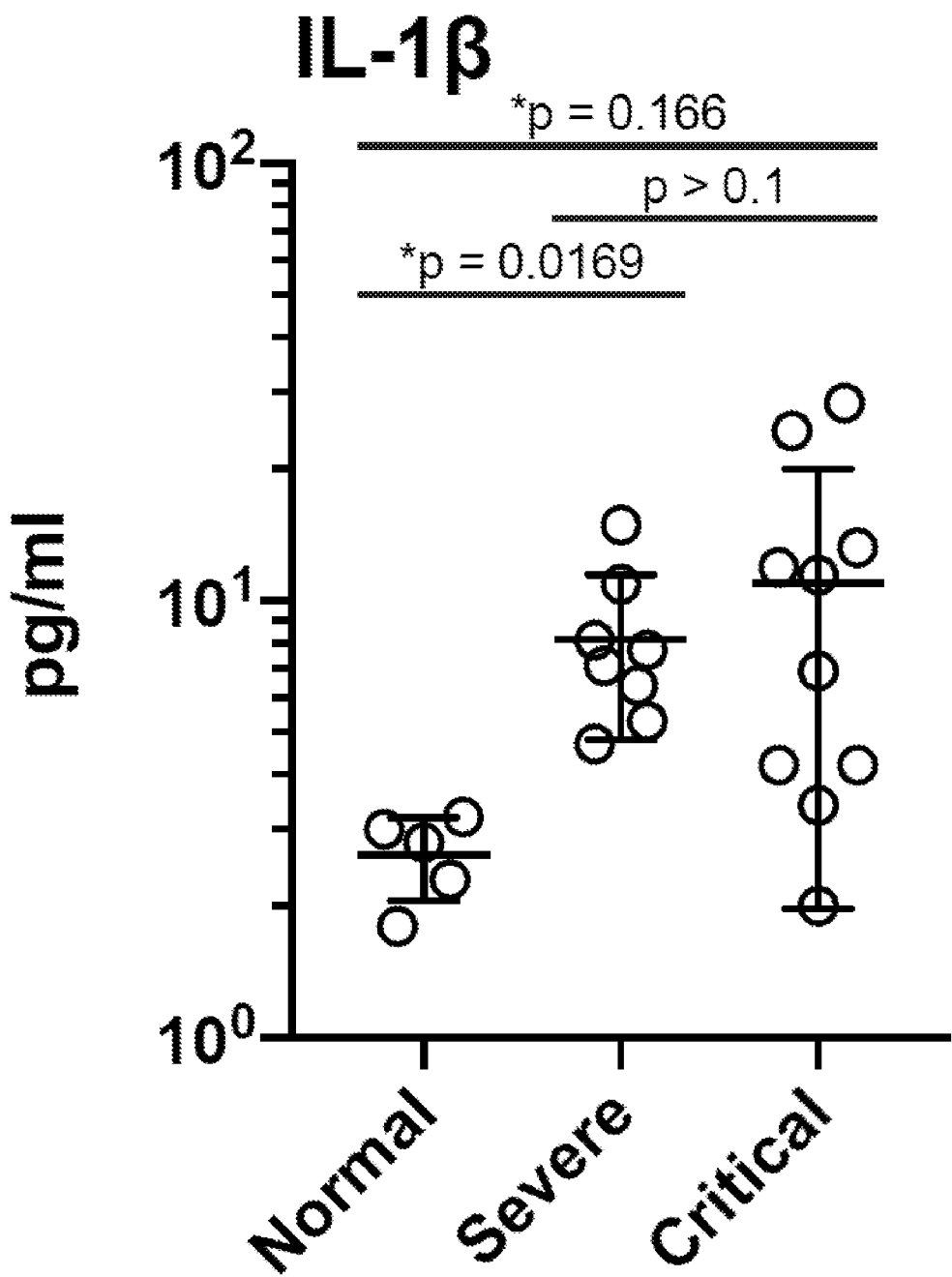
FIGS. 1A-1D provide the extent and phenotype of cytokines and chemokines involved in hypercytokinemia in critical COVID-19. A panel of 38 cytokines/chemokines was tested in plasma from ten COVID-19 patients at Day 0, Day 3 and Day 7 post-leronlimab therapy. All cytokines/chemokines were extremely variable at Day 0 in the 10 critical patients including the IL-1b, IL-6, and IL-8 which are commonly associated with the cytokine storm. Conversely, CCL5/RANTES was significantly elevated in all patients. Seven days post-leronlimab, IL-6 dropped dramatically. Though CCL5/RANTES did not drop as abruptly, blockade of CCR5 by leronlimab as determined by receptor occupancy was close to 100% at day 7 in all patients.

As used herein, the term "severity of a disease" refers to the risk posed by the disease to a subject. Severity of a disease also dictates the extent of treatment necessary for appropriately treating the subject. For example, a disease can be mild, moderate, severe, or critical.

A mild disease may cause slight discomfort and may resolve without any treatment, for example, where a subject's immune system neutralizes the disease. A moderate disease may cause more than slight discomfort and may require some treatment for the disease to resolve. A severe disease causes significant discomfort and would require extensive treatment. A critical disease is life threatening and would require hospitalization and extensive treatment, which may not be successful resulting in the subject's death.

Acute respiratory distress syndrome (ARDS) is a respiratory failure caused by rapid and widespread inflammation in the lungs. In ARDS, fluid builds up in the alveoli thereby preventing the lungs from filling with enough air and reduced oxygen supply to the organs.

Sepsis is a potentially life-threatening condition caused by excessive inflammatory response to an infection. The excessive inflammatory response can trigger changes that can damage multiple organ systems.

Systemic inflammatory response syndrome (SIRS) a widespread inflammatory state affecting the entire body. Unlike sepsis, which is in response to an infection, SIRS can be in response to an infectious or noninfectious insult.

Toxic shock syndrome is a sudden and potentially fatal condition caused by the release of toxins from an infection, such as *Staphylococcus aureus*.

The term "specific binding" refers to a direct association between two molecules, due to, for example, covalent, electrostatic, hydrophobic, and ionic and/or hydrogen-bond interactions, including interactions such as salt bridges and water bridges. A specific binding member describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organization of the other member of the pair of molecules. Thus, the members of the pair have the property of binding specifically to each other. Examples of pairs of specific binding members are antigen-antibody, biotin-avidin, hormone-hormone receptor, receptor-ligand, enzyme-substrate. Specific binding members of a binding pair exhibit high affinity and binding specificity for binding with the each other. Typically, affinity between the specific binding members of a pair is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less.

DETAILED DESCRIPTION

Methods of treating a subject suffering from COVID-19 are provided. Aspects of the methods including administering to the subject an effective amount of an inhibitor of CCR5/CCL5 interaction, such as a CCR5 antagonist. Also provided are methods of assessing severity of a disease involving hypercytokinemia, such as COVID-19, by determining the level of CCL5/RANTES in a subject, as well as compositions for use in such methods.

The disclosure identifies the role of the CCL5/RANTES in the severity of a disease involving hypercytokinemia, particularly, overproduction of immune cells and pro-inflammatory cytokines into the lungs of a subject. The disclosure provides that, relative to controls, an increased level of CCL5/RANTES indicates a more severe form of a disease, whereas a level of CCL5/RANTES comparable to controls indicates a mild form of a disease. Accordingly, certain embodiments of the invention provide a method of assessing the severity of a disease involving hypercytokinemia by determining the level of CCL5/RANTES in a subject. Certain embodiments also provide methods of treating a disease involving hypercytokinemia in a subject by administering an inhibitor of CCL5/RANTES or an inhibitor of CCR5 to the subject having, relative to controls, an increased level of CCL5/RANTES. Further embodiments of the invention provide a device configured to indicate whether the level of CCL5/RANTES in a sample is above or below a predetermined threshold. Even further embodiments of the invention provide a method of treating coronavirus disease 2019 (COVID-19), particularly, a severe or critical form of COVID-19, by administering to a subject an inhibitor of CCL5/RANTES or an inhibitor of CCR5.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.
Methods of Treating Hypercytokinemia Diseases, Including COVID-19

Aspects of the invention include methods of treating a subject suffering from a hypercytokinemia disease, such as COVID-19. The terms "subject," "individual," "host," and "patient," are used interchangeably herein and refer to any mammalian subject for whom diagnosis, treatment, or therapy is desired, particularly humans. By "treatment" it is meant that at least an amelioration of one or more symptoms associated with the condition afflicting the subject is achieved, where amelioration is used in a broad sense to refer to at least a reduction in the magnitude of a parameter, e.g., a symptom associated with the impairment being treated. As such, treatment also includes situations where a pathological condition, or at least symptoms associated therewith, are completely inhibited, e.g., prevented from happening, or stopped, e.g., terminated, such that the adult mammal no longer suffers from the impairment, or at least the symptoms that characterize the impairment. In some instances, "treatment", "treating" and the like refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" may be any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., rejuvenation of tissue or organs, changes in cytokine levels, etc. Treatment of ongoing disease, where the treatment stabilizes or reduces the undesirable clinical symptoms of the patient, occurs in some embodiments. The subject therapy may be administered prior to the symptomatic state of the disease, during the symptomatic stage of the disease, and in some cases after the symptomatic stage of the disease.

By hypercytokinemia disease is meant a disease condition that is characterized by the presence of hypercytokinemia (also known as a cytokine storm). As used herein, hypercytokinemia refers to a severe immune reaction in which the body releases too many cytokines into the blood too quickly. Cytokines play an important role in normal immune responses, but having a large amount of them released in the body all at once can be harmful. Hypercytokinemia can occur as a result of an infection, autoimmune condition, or other disease. It may also occur after treatment with some types of immunotherapy. Signs and symptoms include high fever, inflammation (redness and swelling), and severe fatigue and nausea. Sometimes, hypercytokinemia may be severe or life threatening and lead to multiple organ failure. In embodiments, hypercytokinemia diseases may be caused by a viral infection. In some instances, the hypercytokinemia disease that is treated by methods of the invention is COVID-19, which is caused by SARS-CoV-2 infection. In some instances, the disease, e.g., COVID-19, is severe or critical.

Aspects of the methods of these embodiments include administering to a subject an active agent that inhibits CCR5 mediated CCL5 signaling, such as an inhibitor of CCR5/CCL5 binding interaction. Any convenient active agent may be employed, where active agents include, but are not limited to, CCR5 antagonists/inhibitors, CCL5 antagonists/inhibitors, etc. Furthermore, any convenient type of active agent may be employed, where examples of active agent types include, but are not limited to: small molecules, nucleic acids, specific binding member for CCR5 or CCL5, such as, but not limited to, antibodies, aptamers, peptides, etc.

In some instances, the active agent is a small molecule agent that exhibits the desired activity. Naturally occurring or synthetic small molecule compounds of interest include numerous chemical classes, such as organic molecules, e.g., small organic compounds having a molecular weight of more than 50 and less than about 2,500 Daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below.

In some cases, the active agent is a protein or fragment thereof or a protein complex. In some cases, the active agent is an antibody binding agent or derivative thereof. The term "antibody binding agent" as used herein includes polyclonal or monoclonal antibodies or fragments, that are sufficient to bind to an analyte of interest, e.g., CCR5 or CCL5. The antibody fragments can be, for example, monomeric Fab fragments, monomeric Fab' fragments, or dimeric F(ab)'2 fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies. In some cases, the active agent is an enzyme or enzyme complex. In some cases, the active includes a phosphorylating enzyme, e.g., a kinase. In some cases, the active is a complex including a guide RNA and a CRISPR effector protein, e.g., Cas9, used for targeted cleavage of a nucleic acid.

In some cases, the active agent is a nucleic acid. The nucleic acids may include DNA or RNA molecules. In certain embodiments, the nucleic acids modulate, e.g., inhibit or reduce, the activity of a gene or protein, e.g., by reducing or downregulating the expression of the gene. The nucleic acid may be a single stranded or double-stranded and may include modified or unmodified nucleotides or non-nucleotides or various mixtures and combinations thereof. In some cases, the active agent includes intracellular gene silencing molecules by way of RNA splicing and molecules that provide an antisense oligonucleotide effect or a RNA interference (RNAi) effect useful for inhibiting gene function. In some cases, gene silencing molecules, such as, e.g., antisense RNA, short temporary RNA (stRNA), double-stranded RNA (dsRNA), small interfering RNA (siRNA), short hairpin RNA (shRNA), microRNA (miRNA), tiny non-coding RNA (tncRNA), snRNA, snoRNA, and other RNAi-like small RNA constructs, may be used to target a protein-coding as well as non-protein-coding genes. In some case, the nucleic acids include aptamers (e.g., spiegelmers). In some cases, the nucleic acids include antisense compounds. In some cases, the nucleic acids include molecules which may be utilized in RNA interference (RNAi) such as double stranded RNA including small interfering RNA (siRNA), locked nucleic acid (LNA) inhibitors, peptide nucleic acid (PNA) inhibitors, etc.

As described above, in some instances the active agent employed in embodiments of methods of the invention is a CCR5 targeting agent, such as a CCR5 inhibitor/antagonist. CCR5 targeting agents are described in U.S. Patent Application Pub. Nos. 1 20180303830, 20170231991, 20140109245, and 20130303512; the disclosures of which are incorporated herein by reference in their entirety. Useful drugs targeting CCR5 may, in some instances, include CCR5 antagonists, such as but not limited to e.g., small molecule (including peptide and non-peptide small molecule) inhibitors, antibodies, and the like. Non-limiting examples of CCR5 antagonists include: Maraviroc (aka Selzentry or Celsentri), INCB-9471 ((4,6-dimethylpyrimidin-5-yl)[4-[(3S)-4-[(1R,2R)-2-ethoxy-5-(trifluoromethyl)-2,3-dihydro-1H-inden-1-yl]-3-methylpiperazin-1-yl]-4-methylpiperidin-1-yl]methanone; orally available CCR5 antagonist; PubChem CID: 49871007), Leronlimab (PRO-140, a humanized monoclonal antibody directed against CCR5), Aplaviroc (4-(4-{[(3R)-1-butyl-3-[(R)-cyclohexyl(hydroxy)methyl]-2,5-dioxo-1,4,9-triazaspiro[5.5]undecan-9-yl]methyl}phenoxy)benzoic acid; a potent noncompetitive allosteric antagonist of the CCR5 receptor), Vicriviroc (5-{4-[(3S)-4-[(1R)-2-methoxy-1-[4-(trifluoromethyl)-phenyl]ethyl]-3-methylpiperazin-1-yl]-4-methylpiperidine-1-carbonyl}-4,6-dimethylpyrimidine; CCR5 entry inhibitor previously named SCH 417690 and SCH-D), fully human monoclonal antibodies to CCR5 (such as the HGS004 as described by Lalezari et al., J Infect Dis. (2008) 197(5):721-7), and the like.

In some instances, the active agent is an antibody that binds to CCR5. An antibody that specifically binds to CCR5 can be polyclonal or monoclonal antibody or fragments that are sufficient to bind CCR5. The antibody fragments can be, for example, monomeric Fab fragments, monomeric Fab' fragments, or dimeric F(ab)'$_2$ fragments, single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies. An antibody that specifically binds to CCR5 can be a humanized monoclonal antibody, such as Leronlimab (PRO 40), PA14, 2D7, RoAb13, RoAb14, 45523. Certain examples of CCR5 antibodies are described by the reference Olson et al. *Curr Opin HIV AIDS,* 2009 March; 4(2):104-111, which is herein incorporated by reference in its entirety. In some instances, the active agent is Leronlimab. In some instances, the active agent is a small molecule inhibitor of CCR5, such as but not limited to: Maraviroc, vicriviroc, aplaviroc, SCH-C, or TAK-779.

In some embodiments, the active agent targets CCL5/RANTES. In certain embodiments, an inhibitor of CCL5/RANTES is employed as the active agents, where inhibitors of interest include, but are not limited to: small molecules, nucleic acids, specific binding members for CCL5/RANTES, such as an antibody, aptamer, or a peptide, etc., such as described above. An example of an inhibitor of CCL5/RANTES is Met-CCL5. Further examples of RANTES/CCL5 inhibitors that may be employed in embodiments of the invention include, but are not limited to, those described in United States Published Application Publication Nos. 20050220790, 20060165650, 20090148455, 20120077733, 20120201826, 20140377278, and 20150079099, the disclosures of which are herein incorporated by reference.

Where desired, active agents may be administered to a subject as a pharmaceutical composition. Pharmaceutical compositions formulated for topical administration may include ointments, lotions, creams, gels, drops, sprays, liquids, salves, sticks, soaps, aerosols, and powders. Any conventional pharmaceutical excipient, such as carriers, aqueous, powder or oily bases, thickeners and the like may be used. Ointments and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or coloring agents. Powders may be formed with the aid of any suitable powder base. Drops may be formulated with an aqueous or non-aqueous base also comprising one or more dispersing, solubilizing or suspending agents. Aerosol sprays are conveniently delivered from pressurized packs, with the use of a suitable propellant.

In practicing embodiments of the invention, active agent compositions may be administered according to any desired dosage, such as once per day, a few or several times per day, or even multiple times per day, depending upon, among other things, the indication being treated and the judgment of the prescribing physician. For example, in some instances, compositions that include one or more active agents may be administered once per day, a few or several times per day, or even multiple times per day, depending upon, among other things, the indication being treated and the judgment of the prescribing physician.

Depending on whether systemic and/or local treatment is chosen, methods of administration may be chosen depending also on the condition being treated and the pharmaceutical composition being administered. Administration of an effective amount (in one or multiple doses) of the subject agent(s) can be done in a variety of ways, including, but not limited to, subcutaneously, intravenously, intraperitoneally, intramuscularly, and direct injection to specified organs or tumors, systemic administration, etc. Administration of the pharmaceutical compositions may be through a single route or concurrently by several routes. As such, the active agent can be administered to a subject via a suitable route of administration and include oral, mucosal (e.g., nasal, sublingual, vaginal, buccal, or rectal), parenteral (e.g., subcutaneous, intravenous, bolus injection, intramuscular, or intra-arterial, intraperitoneal), or transdermal.

As described above, in some instances that active agent is an anti-CCR5 antibody, such as Leronlimab (PRO 140). In such embodiments, the antibody active agent is administered with a pharmaceutically acceptable carrier. Such pharmaceutically acceptable carriers may include but are not limited to aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline, and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases, and the like.

The dose of the composition of the invention will vary depending on the subject and upon the particular route of administration used. Dosages can range from 0.1 g/kg to 100,000 g/kg. In another embodiment the antibody or binding fragment thereof is formulated to deliver between 100 mg/mL to 200 mg/mL of the antibody or binding fragment thereof to the subject. In another embodiment the antibody or binding fragment thereof is formulated to deliver between 100 mg/mL to 150 mg/mL of the antibody or binding fragment thereof to the subject. In another embodiment the antibody or binding fragment thereof is formulated to deliver between 150 mg/mL to 200 mg/mL of the antibody or binding fragment thereof to the subject. In another embodiment the antibody or binding fragment thereof is formulated to deliver 175 mg/mL of the antibody or binding fragment thereof to the subject. Based upon the composition, the dose can be delivered continuously, such as by continuous pump, or at periodic intervals, e.g., on one or more separate occasions. Desired time intervals of multiple doses of a particular composition can be determined without undue experimentation by one skilled in the art.

In one embodiment of the instant methods, the antibody or binding fragment thereof is administered to the subject a plurality of times, and each administration delivers from 0.01 mg per kg body weight to 50 mg per kg body weight of the antibody or binding fragment thereof to the subject. In another embodiment, each administration delivers from 0.05 mg per kg body weight to 25 mg per kg body weight of the antibody or binding fragment thereof to the subject. In a further embodiment, each administration delivers from 0.1 mg per kg body weight to 10 mg per kg body weight of the antibody or binding fragment thereof to the subject. In a still further embodiment, each administration delivers from 0.5 mg per kg body weight to 5 mg per kg body weight of the antibody or binding fragment thereof to the subject. In another embodiment, each administration delivers from 1 mg per kg body weight to 3 mg per kg body weight of the antibody or binding fragment thereof to the subject. In another embodiment, each administration delivers about 2 mg per kg body weight of the antibody or binding fragment thereof to the subject.

In an embodiment, the antibody or binding fragment thereof is administered in a formulation comprising 175 mg/mL of the anti-CCR5 binding agent and may be delivered in two 1 mL shots for administration of about 350 mg in total to a subject in need thereof.

In one embodiment, the antibody or binding fragment thereof is administered a plurality of times, and a first administration is separated from the subsequent administration by an interval of less than one week. In another embodiment, the first administration is separated from the subsequent administration by an interval of at least one week. In a further embodiment, the first administration is separated from the subsequent administration by an interval of one week. In another embodiment, the first administration is separated from the subsequent administration by an interval of two to four weeks. In another embodiment, the first administration is separated from the subsequent administration by an interval of two weeks. In a further embodiment, the first administration is separated from the subsequent administration by an interval of four weeks. In yet another embodiment, the antibody or binding fragment thereof is administered a plurality of times, and a first administration is separated from the subsequent administration by an interval of at least one month.

In a further embodiment, the antibody or binding fragment thereof is administered to the subject via intravenous infusion. In another embodiment, the antibody or binding fragment thereof is administered to the subject via subcutaneous injection. In another embodiment, the antibody or binding fragment thereof is administered to the subject via intramuscular injection.

Those of skill in the art will readily appreciate that dose levels can vary as a function of the specific compound, e.g., small molecule, antibody, nucleic acid, etc., the nature of the delivery vehicle, and the like. Preferred dosages for a given compound are readily determinable by those of skill in the art by a variety of means.

In those embodiments where an effective amount of an active agent is administered to the adult mammal, the amount or dosage is effective when administered for a suitable period of time so as to evidence a reduction in one or more symptoms of the target disease. In some instances, an effective amount or dose of active agent will not only slow or halt the progression of the disease condition but will also induce the reversal of the condition, i.e., will cause an improvement the subject's condition. Where desired, effectiveness of treatment may be assessed using any convenient protocol. Biochemically, by an "effective amount" or "effective dose" of active agent is meant an amount of active agent that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances reverse, one or more target symptoms of the disease condition.

In certain embodiments, methods of treating a subject for a hypercytokinemia disease, e.g., Covid-19, include methods of assessing the severity of a disease involving hypercytokinemia, such as methods of assessing as described below.

Methods of Assessing a Disease Involving Hypercytokinemia

As summarized above, certain embodiments of the invention provide a method of assessing the severity of a disease involving hypercytokinemia in a subject, the method comprising:

(a) determining the level of CCL5/RANTES in a test sample obtained from the subject, and (b) assessing the severity of the disease based on the determined level of CCL5/RANTES in the test sample.

As discussed above, hypercytokinemia is a potentially fatal immune reaction and involves a positive feedback loop between cytokines and immune cells, which causes in the body highly elevated levels of various cytokines. Hypercytokinemia is also referenced as "cytokine storm." Hypercytokinemia typically involves increased concentration of cytokines, such as interferons, interleukins, chemokines, colony-stimulating factors, and tumor necrosis factors. Such immune dysregulation can be an underlying factor in mortality resulting from many infections.

In certain embodiments, the disease involving hypercytokinemia further comprises an overproduction of immune cells and/or pro-inflammatory cytokines into the lungs of the subject. Hypercytokinemia may result in excessive inflammatory response in the lungs, which typically occurs in the infections in the lungs or other organs. Such excessive inflammatory response in the lung includes infiltration into the lungs by immune cells as well as excessive secretion of proinflammatory cytokines in the lungs, which in turn attracts more immune cells into the lungs. Thus, hypercytokinemia can also involve positive-feedback loop between activated cells and released cytokines.

Assessing the severity of the disease may involve comparing the determined level of CCL5/RANTES in the test sample with the level of CCL5/RANTES in a control sample or a reference value.

A control sample can be obtained from one or more of the following: an individual belonging to the same species as the subject and not having the disease; an individual belonging to the same species as the subject and known to have the disease with known level of severity, for example, asymptomatic, mild, moderate, severe, or critical; or the subject prior to having the disease. If a control sample is obtained from a healthy individual and the level of CCL5/RANTES in the test sample is significantly higher than that of the control sample, particularly, higher than that of the control sample by: between 2 fold and 200 fold; between 10 fold and 150 fold, between 20 fold and 100 fold, or between 40 fold and 60 fold, the extent of the increase in the level of CCL5/RANTES in the test sample could be used to assess the severity of the disease in the subject.

Figure 1B:
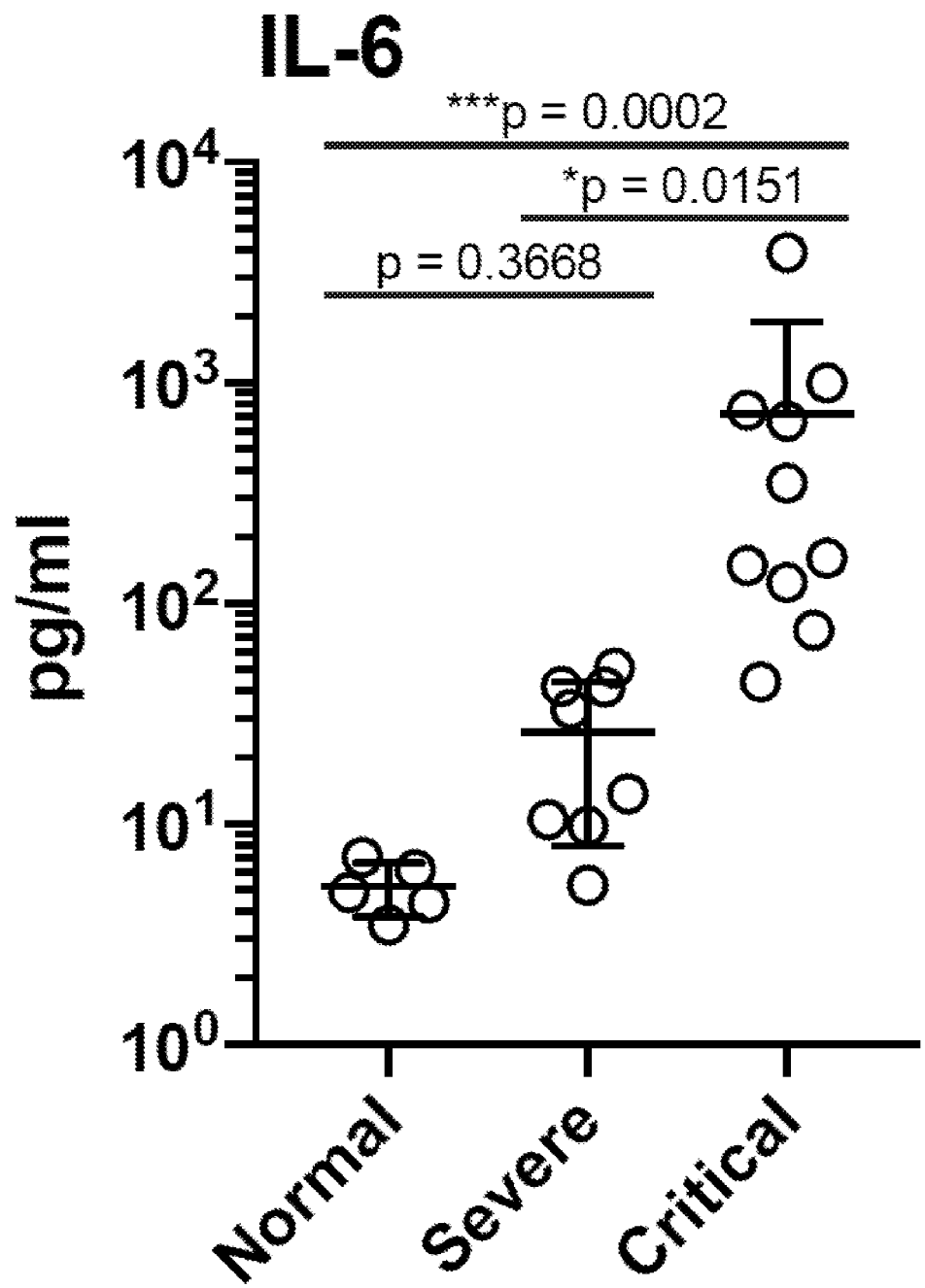
Figure 1C:
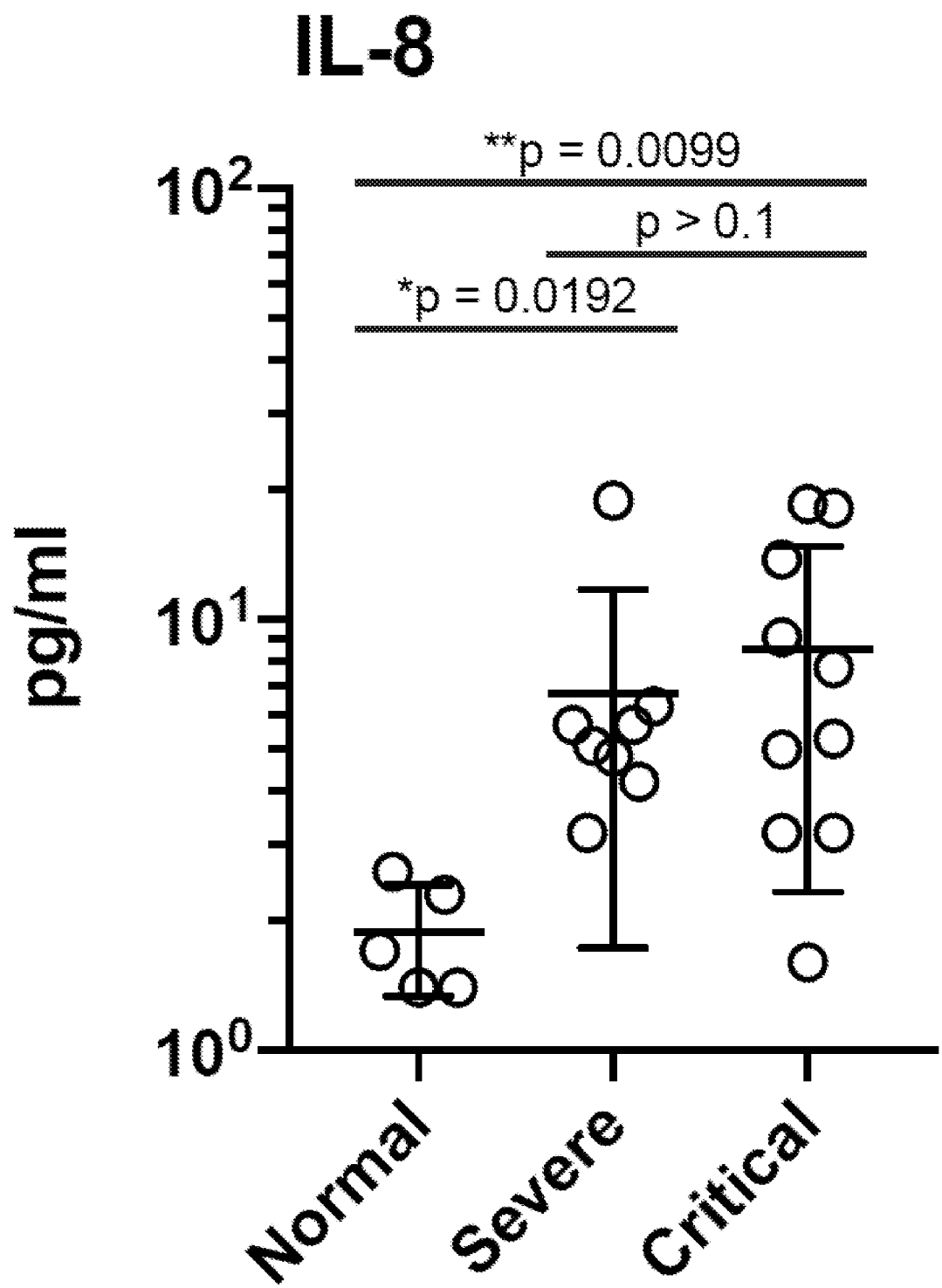
Figure 1D:
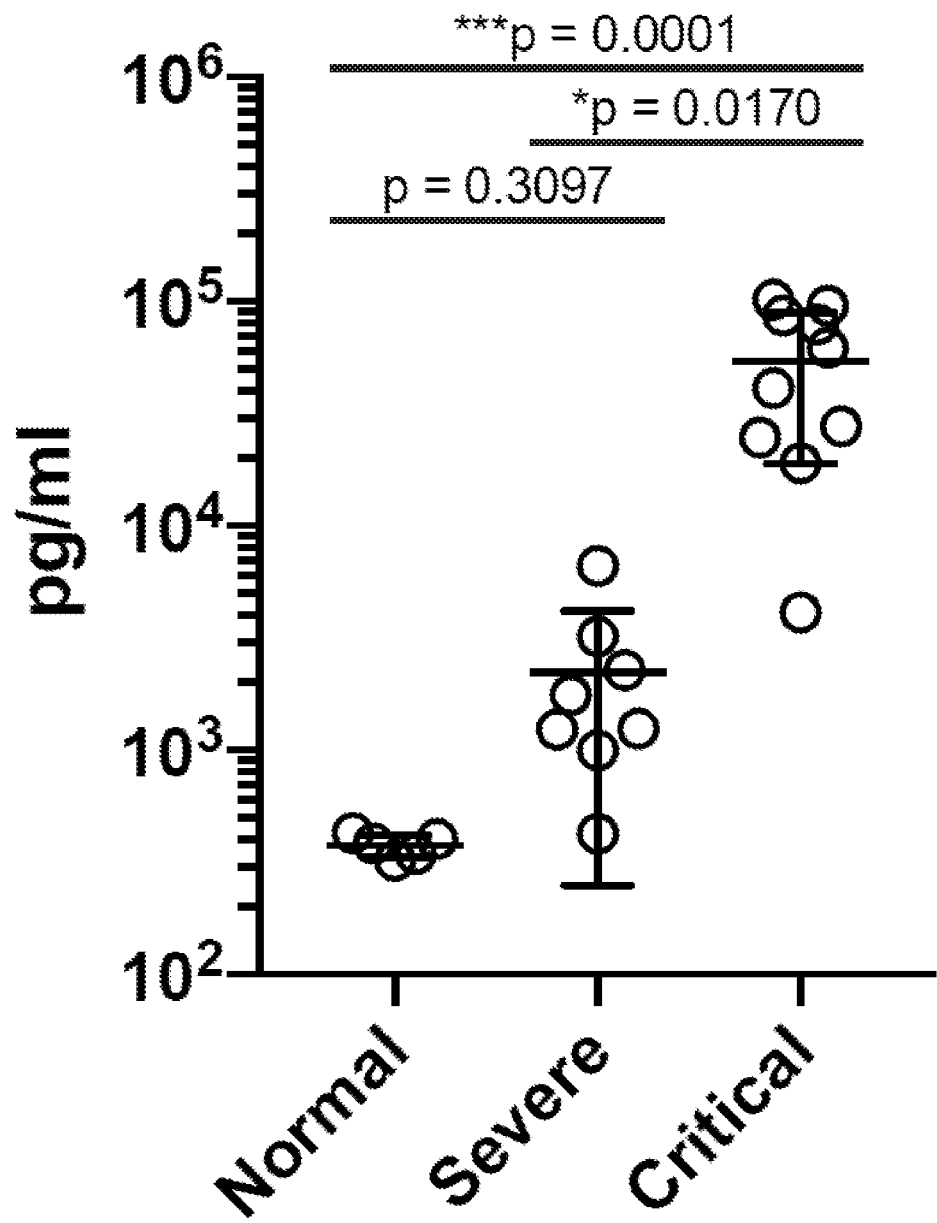

For example, as provided in FIG. 1D, an increase of between at least about 6 fold and at least about 20 fold in the CCL5/RANTES level in a test plasma sample compared to a control sample could indicate that the subject has a severe form of COVID-19; whereas, an increase of between at least about 60 fold and at least about 300 fold in the CCL5/RANTES level in a test plasma sample compared to a control sample could indicate that the subject has a critical form of COVID-19.

For a particular disease involving hypercytokinemia, a person of ordinary skill in the art can determine the difference in the CCL5/RANTES level in a control sample and in a test sample that indicates different levels of severity of the disease.

The control sample and the test sample can be obtained from the same type of an organ or tissue. The organ or tissue can be brain, eyes, pineal gland, pituitary gland, thyroid gland, parathyroid glands, thorax, heart, lung, esophagus, thymus gland, pleura, adrenal glands, appendix, gall bladder, urinary bladder, large intestine, small intestine, kidneys, liver, pancreas, spleen, stoma, ovaries, uterus, or skin. The control sample and the test sample can also be obtained from the same type of a body fluid. The body fluid can be aqueous humor, vitreous humor, bile, blood, cerebrospinal fluid, chyle, endolymph, perilymph, lymph, mucus, pericardial fluid, peritoneal fluid, pleural fluid, pus, rheum, saliva, sputum, synovial fluid, blood, serum or plasma.

A reference value corresponding to the level of CCL5/RANTES may indicate the level of CCL5/RANTES associated with severity of the disease, such as mild, moderate, severe, or critical form of a disease. As such, a reference value corresponding to level of CCL5/RANTES may represent the level of CCL5/RANTES in a subject who has mild, moderate, severe, or critical form of a disease.

For example, when the disease is COVID-19, the reference value can be: 200 pg/ml, 250 pg/ml; 300 pg/ml, 350 pg/ml or 400 pg/ml (which would indicate the absence of disease); or about: 1 ng/ml, 2 ng/ml, 3 ng/ml, 4 ng/ml, 5 ng/ml, 6 ng/ml, 7 ng/ml, 8 ng/ml, 9 ng/ml, 10 ng/ml (which would indicate severe form of COVID-19); or: 15 ng/ml, 20 ng/ml, 25 ng/ml, 30 ng/ml, 35 ng/ml, 40 ng/ml, 45 ng/ml, 50 ng/ml, 55 ng/ml, 60 ng/ml (which could indicate critical form of COVID-19). Therefore, if the CCL5/RANTES level in a test sample from a subject is 50 ng/ml, one could assess that the subject is suffering from or could develop a critical form of COVID-19. On the other hand, if CCL5/RANTES level in a test sample from a subject is 8 ng/ml, one could assess that the subject is suffering from or could develop a severe form of COVID-19. Further, if CCL5/RANTES level in a test sample from a subject is 200 pg/ml, one could assess that the subject does not have COVID-19 or has asymptomatic or mild form of COVID-19.

A person of ordinary skill in the art can obtain appropriate reference values based on the disease being examined and such information can be obtained from the well-known sources in the relevant art or generated based on the testing conducted on a case by case basis.

If the disease is COVID-19, the disease can be asymptomatic, mild, moderate, severe, or critical. An asymptomatic form of COVID-19 does not show any symptoms in the subject. A mild form of COVID-19 may show mild form of one or more of: tiredness, fever, cough, breathlessness after moderate exercise, sore throat, muscle ache, headache, and diarrhea. Mild form of COVID-19 may not require management of symptoms. A moderate form of COVID-19 may show moderate form of one or more of: tiredness, fever, cough, breathlessness after slight activity, sore throat, muscle ache, headache, and diarrhea. Moderate form of COVID-19 may require managing the symptoms. A severe form of COVID-19 may show of one or more of: severe tiredness, high fever, cough, breathlessness even at rest, painful breathing, loss of appetite, loss of thirst, sore throat, muscle ache, headache, diarrhea, and confusion. Severe form of COVID-19 would typically require significant intervention for managing symptoms, such as: pneumonia, hypoxemic respiratory failure, ARDS, sepsis, septic shock, cardiomyopathy, arrhythmia, acute kidney injury, and complications from prolonged hospitalization including secondary bacterial infections, thromboembolism, gastrointestinal bleeding, and critical illness polyneuropathy/myopathy.

A critical form of COVID-19 may show of one or more of: severe tiredness, high fever, cough, breathlessness even at rest, painful breathing, loss of appetite, loss of thirst, sore throat, muscle ache, headache, diarrhea, confusion, severe pneumonia, ARDS, sepsis, organ failure, coma, and death. Critical form of COVID-19 requires hospitalization for managing symptoms such as: pneumonia, ARDS, sepsis, septic shock, cardiomyopathy, arrhythmia, acute kidney injury, and complications from prolonged hospitalization including secondary bacterial infections, thromboembolism, gastrointestinal bleeding, and critical illness polyneuropathy/myopathy. Ventilator assisted breathing may be required.

A disease involving hypercytokinemia can be an inflammatory disease or an infection. An inflammatory disease can be an autoimmune disease, graft rejection, multiple sclerosis, pancreatitis, or multiple organ dysfunction syndrome. A disease involving hypercytokinemia can also be an infection, such as a viral, bacterial, fungal, or parasitic infection. Additional examples of infections that can cause a disease involving hypercytokinemia are known in the art and severity of such diseases can be assessed according to the methods disclosed herein. A bacterial infection can comprise bacteremia, bacterial sepsis, pneumonia, cellulitis, meningitis, erysipelas, infective endocarditis, necrotizing fasciitis, prostatitis, pseudomembranous colitis, pyelonephritis, or septic arthritis. A bacterial infection can be caused by a *Streptococcus* spp., *Staphylococcus* spp., *Salmonella* spp., *Pseudomonas* spp., *Clostridium* spp., *Vibrio* spp., *Mycobacterium* spp. or *Haemophilus* spp. Additional examples of bacteria that can cause a disease involving hypercytokinemia are known in the art and severity of such bacterial infections can be assessed according to the methods disclosed herein. A viral infection can be caused by a coronavirus, influenza virus, Epstein-Barr virus, Human Immunodeficiency Virus, Ebola virus, retrovirus, or variola virus. The coronavirus can be severe acute respiratory syndrome coronavirus 2 (SARS-CoV-2). Additional examples of viruses that can cause a disease involving hypercytokinemia are known in the art and severity of such viral infections can be assessed according to the methods disclosed herein. A disease involving hypercytokinemia can also comprise ARDS, sepsis, SIRS, or toxic shock syndrome.

Any convenient method of determining CCL5/RANTES in a same may be employed, where various methods of determining CCL5/RANTES in a sample are known in the art and can be used in the methods disclosed herein. Certain such methods include flow cytometry, mass spectrometry, protein array analysis, Western blot analysis, enzyme-linked immunosorbent assay (ELISA), or radio-immune assay (RIA).

In certain embodiments, determining the level of CCL5/RANTES is performed by flow cytometry. Flow cytometry is a methodology using multi-parameter data for identifying and distinguishing between different particle (e.g., bead) types i.e., particles that vary from one another in terms of label (wavelength, intensity), size, etc., in a fluid medium. In flow cytometrically analyzing a sample, an aliquot of the sample is first introduced into the flow path of the flow cytometer. When in the flow path, the particles in the sample are passed substantially one at a time through one or more sensing regions, where each of the cells is exposed separately and individually to a source of light at a single wavelength (or in some instances two or more distinct sources of light) and measurements of cellular parameters, e.g., light scatter parameters, and/or marker parameters, e.g., fluorescent emissions, as desired, are separately recorded for each cell. The data recorded for each cell is analyzed in real time or stored in a data storage and analysis means, such as a computer, for later analysis, as desired.

In flow cytometry-based methods, particles, e.g., beads, are passed, in suspension, substantially one at a time in a flow path through one or more sensing regions where in each region each cell is illuminated by an energy source. The energy source may include an illuminator that emits light of a single wavelength, such as that provided by a laser (e.g., He/Ne or argon) or a mercury arc lamp or an LED with appropriate filters. For example, light at 488 nm may be used as a wavelength of emission in a flow cytometer having a single sensing region. For flow cytometers that emit light at two distinct wavelengths, additional wavelengths of emission light may be employed, where specific wavelengths of interest include, but are not limited to: 405 nm, 535 nm, 561 nm, 635 nm, 642 nm, and the like. Following excitation of a labeled specific binding member bound to a polypeptide by an energy source, the excited label emits fluorescence and the quantitative level of the polypeptide on each cell may be detected, by one or more fluorescence detectors, as it passes through the one or more sensing regions.

In flow cytometry, in addition to detecting fluorescent light emitted from particles labeled with fluorescent markers, detectors, e.g., light collectors, such as photomultiplier tubes (or "PMT"), an avalanche photodiode (APD), etc., are also used to record light that mediated by, e.g., emitted by a label on, the particle. Flow cytometers may further include one or more electrical detectors. In certain embodiments, an electrical detector may be employed for detecting a disturbance caused by a particle passing through an electrical field propagated across an aperture in the path of the particles. Such flow cytometers having electrical detectors will contain a corresponding electrical energy emitting source that propagates an electrical field across the flow path or an aperture through which cells are directed. Any convenient electrical field and/or combination of fields with appropriate detector(s) may be used for the detection and/or measurement of particles passing through the field including but not limited to, e.g., a direct current electrical field, alternating current electrical field, a radio-frequency field, and the like.

Flow cytometers further include data acquisition, analysis and recording means, such as a computer, wherein multiple data channels record data from each detector for each cell as it passes through the sensing region. The purpose of the analysis system is to classify and count cells wherein each cell presents itself as a set of digitized parameter values and to accumulate data for the sample as a whole.

The flow cytometry can comprise a bead-based assay, such as a sandwich protocol for bead based assay. In one embodiment, determining the level of CCL5/RANTES by flow cytometry comprises contacting the sample with a bead comprising an antibody that specifically binds to CCL5/RANTES, washing the bead and contacting the washed bead with a fluorescently labeled secondary antibody that specifically binds to CCL5/RANTES, washing the bead and detecting the presence of CCL5/RANTES on the bead by detecting by flow cytometry the label on the bead.

In a specific embodiment, determining the level of CCL5/RANTES by flow cytometry comprises contacting the sample with a bead comprising an antibody that specifically binds to CCL5/RANTES, washing the bead and contacting the washed bead with a biotinylated secondary antibody that specifically binds to CCL5/RANTES, washing the bead and contacting the washed bead with a fluorescently labeled streptavidin, and detecting the presence of CCL5/RANTES on the bead by detecting by flow cytometry the fluorescent label on the bead. In some instances, the assay employed is BioLegend's LEGENDplex™ bead-based immunoassay (BioLegend, San Diego, Calif.).

The fluorescent label used to detect the bead can be selected from a large number of dyes that are commercially available from a variety of sources, such as Molecular Probes (Eugene, Oreg.) and Exciton (Dayton, Ohio). Examples of fluorophores of interest include, but are not limited to, 4-acetamido-4'-isothiocyanatostilbene-2,2'disulfonic acid; acridine and derivatives such as acridine, acridine orange, acridine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumarin 151); cyanine and derivatives such as cyanosine, Cy3, Cy5, Cy5.5, and Cy7; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; or combinations thereof. Other fluorophores or combinations thereof known to those skilled in the art may also be used, for example those available from Molecular Probes (Eugene, Oreg.) and Exciton (Dayton, Ohio).

Also of interest as specific binding members are those nucleic acid dyes or stains containing intrinsic fluorescence including those that specifically label DNA. Dyes and stains that are specific for DNA (or preferentially bind double stranded polynucleotides in contrast to single-stranded polynucleotides) and therefore may be employed as non-specific stains include, but are not limited to: Hoechst 33342 (2'-(4-Ethoxyphenyl)-5-(4-methyl-1-piperazinyl)-1H,1'H-2,5'-bibenzimidazole trihydrochloride) and Hoechst 33258 (4-[6-(4-Methyl-1-piperazinyl)-1',3'-dihydro-1H,2'H-2,5'-bibenzimidazol-2'-ylidene]-2,5-cyclohexadien-1-one trihydrochloride) and others of the Hoechst series; SYTO 40, SYTO 11, 12, 13, 14, 15, 16, 20, 21, 22, 23, 24, 25 (green); SYTO 17, 59 (red), DAPI, DRAQ5™ (an anthraquinone dye with high affinity for double stranded DNA), YOYO-1, propidium iodide, YO-PRO-3, TO-PRO-3, YOYO-3 and TOTO-3, SYTOX Green, SYTOX, methyl green, acridine homodimer, 7-aminoactinomycin D, 9-amino-6-chloro-2-methoxyactridine.

In certain embodiments, determining the level of CCL5/RANTES is performed by ELISA. ELISA can be direct ELISA, indirect ELISA, competitive ELISA, or sandwich ELISA. Various methods of conducting ELISA assay are known in the art and can be used in the methods disclosed herein. An example of such an assay is the Quantikine® ELISA Human CCL5/RANTES Immunoassay (RnD Systems, Inc.).

Additional methods of determining plasma CCL5/RANTES level are described in Published United States Patent Application Publication No. 20120238460, the disclosure of which is herein incorporated by reference.

As such, certain embodiments of the invention provide a method comprising: assaying the level of CCL5/RANTES in a sample obtained from a subject suffering from a disease involving hypercytokinemia. Such methods can further comprise assaying the level of CCL5/RANTES in a control sample and/or obtaining one or more reference values corresponding to the level of CCL5/RANTES. The details of control samples and reference values discussed above are applicable to the methods of assaying CCL5/RANTES. A sample for assaying the level of CCL5/RANTES can be obtained from a subject suffering from various diseases discussed above. Moreover, various methods discussed above could be used for assaying the level of CCL5/RANTES in a sample.

In certain embodiments, the methods of assaying the level of CCL5/RANTES in a sample obtained from a subject further comprises treating the subject for the disease. Certain such embodiments comprise treating a subject by administering to the subject an inhibitor of CCL5/RANTES or an inhibitor of CCR5, e.g., as described above. In some embodiments, such disease is a severe or critical form of COVID-19. Various therapeutic methods discussed above, particularly, various inhibitors of CCL5/RANTES or CCR5 discussed above can be used in the methods of treating a subject discussed herein.

Devices for Assaying the Level of CCL5/Rantes

Further embodiments of the invention provide a device configured to indicate whether the level of CCL5/RANTES in a sample is above or below a predetermined threshold.

In certain such embodiments, the device is a flow cytometer. The flow cytometer can comprise a signal processing unit that is configured to indicate whether the level of CCL5/RANTES in a sample is above or below a predetermined threshold. Such signal processing unit can comprise a physical computer-readable medium comprising instructions that, when executed, indicate whether the level of CCL5/RANTES in a sample is above or below a predetermined threshold.

The predetermined threshold for CCL5/RANTES level can be about: 200 pg/ml, 250 pg/ml, 300 pg/ml, 350 pg/ml, 400 pg/ml, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 35 ng/ml, 40 ng/ml, 45 ng/ml, 50 ng/ml, 55 ng/ml, or 60 ng/ml.

In certain such embodiments, the device comprises an internal control that provides a signal corresponding to the CCL5/RANTES level at the predetermined threshold. Accordingly, a signal intensity higher than that of the internal control would indicate that the level of CCL5/RANTES in the tested sample is higher than the predetermined threshold, whereas, a signal intensity lower than that of the internal control would indicate that the level of CCL5/RANTES in the tested sample is lower than the predetermined threshold.

In some cases, the device is provided with a separate container containing a control having CCL5/RANTES at a concentration of the predetermined threshold.

The following example(s) is/are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

Example 1

CCL5/RANTES Levels in Severe Cases of COVID-19

This Example demonstrates that patients with severe COVID-19 have significantly reduced CD8 T-effector cells and to a lesser extent CD4 T-helper cells. In addition, the predominant cytokines in hypercytokinemia or cytokine storm including IL-1β, IL-8, IL-6 were quantified in patients with severe COVID-19. Also, CCL5/RANTES is upregulated in severe COVID-19 patients to an extent much greater than the other molecules more commonly associated with COVID-19 infection. Because CCL5/RANTES contributes to the immunopathogenesis of COVID-19 lung disease and that CCL5/RANTES is involved in acute renal disease which is common in these patients, blocking CCL5/RANTES can be used to treat COVID-19, particularly, a severe form of COVID-19.

1. Reduced CD8 T-cell Percentages in Critical COVID-19 Patients

To elucidate the immune status and response to infection in 10 critical COVID-19 patients (Table 1), routine immunophenotyping was performed from samples drawn at Day 0, Day 3, and Day 7. In all ten patients, CD8 percentages were significantly decreased compared to normal levels, To further determine the possible cause of this profound immunosuppression, high parameter flow cytometer analysis was performed using immune subpopulation and immune function markers. These analyses demonstrated significant immune exhaustion as evidenced by increased PD-1 expression on CD8 and CD4 T-cells as well as increased expression of LAG-3, and cleaved caspase 3 (CC3). Following administration of 700 mg of the anti-CCR5 humanized monoclonal antibody Leronlimab, all ten patients exhibited improvements in exhaustion markers and by Day 7 the immune profiles resembled the normal control blood.

2. Characterization and Quantification of Plasma Cytokines/Chemokines-Predominance of CCL5

To determine the extent and phenotype of "cytokine storm" cytokines and chemokines in critical COVID-19, a panel of 38 cytokines/chemokines was quantified in plasma from the ten critical COVID-19 patients at Day 0, Day 3 and Day 7 post-leronlimab therapy. All cytokines/chemokines were extremely variable at Day 0 in the 10 critical patients including the IL-1b, IL-6, and IL-8 which are commonly associated with the cytokine storm (FIGS. 1A-1C). Conversely, CCL5/RANTES was significantly elevated in all patients (FIG. 1D). Seven days post-leronlimab, IL-6 dropped dramatically. Though RANTES did not drop as abruptly, blockade of CCR5 by leronlimab as determined by receptor occupancy was close to 100% at day 7 in all patients.

Table 1 below provides representative normal cytokine levels.

TABLE 1

|  | IL-1b | IL-6 | IL-8 | RANTES |
| --- | --- | --- | --- | --- |
| nl 1 | 3.2 | 6.2 | 2.3 | 345 |
| nl 2 | 2.8 | 4.9 | 1.4 | 402 |
| nl 3 | 2.3 | 3.5 | 1.7 | 322 |
| nl 4 | 3 | 7.1 | 1.4 | 427 |
| nl 5 | 1.8 | 4.4 | 2.6 | 383 |
| nl 6 | 1.6 | 5 | 1.1 | 325 |
| nl 7 | 3.4 | 7.8 | 1.9 | 379 |
| nl 8 | 3.6 | 3.6 | 2.3 | 356 |
| nl 9 | 1.2 | 4.1 | 1.4 | 413 |
| nl 10 | 2.8 | 6.3 | 2.5 | 391 |

Table 2 below provides cytokine levels from COVID-019 samples.

TABLE 2

| COVID SAMPLES | IL-1b | IL-6 | IL-8 | RANTES |
| --- | --- | --- | --- | --- |
| 1 | 8.1 | 41.9 | 5.1 | 423 |
| 2 | 14.9 | 51.1 | 18.9 | 3201 |
| 3 | 7.7 | 10.5 | 5.7 | 1242 |
| 4 | 10.9 | 33.1 | 3.2 | 1234 |
| 5 | 6.4 | 5.3 | 4.8 | 996 |
| 6 | 5.3 | 42.1 | 5.7 | 6608 |
| 7 | 4.7 | 13.7 | 6.3 | 2278 |
| 8 | 7.1 | 9.8 | 4.2 | 1756 |

3. Use of CCL5/RANTES in Assessing Severity of COVID-19 and Treatment

The worldwide pandemic due to COVID-19 has prompted the investigation of numerous therapies broadly categorized as either anti-viral agents or approaches that temper the "Cytokine Storm." Neither of these approaches addresses directly the profound immunosuppression and almost all of these agents lack the ability to address both viral replication and immune dysfunction. Further, approaches to quiet the cytokine storm have been piecemeal, inhibiting one component such as IL-6 but not simultaneously inhibiting the other components such as IL-1b, IL-8, and GM-CSF.

The results disclosed herein show that the predominant component of the Cytokine Storm, CCL5/RANTES, can be targeted using a leronlimab which but virtue of controlling immune trafficking of CCR5 expressing cells and repolarization of macrophages also reduces IL-6 and restores immune homeostasis.

The hallmark of the first reports of COVID-19 was the "cytokine storm" that leads to the lung pathology, ARDS, and in some cases death. While other studies are focused on the high levels of IL-6, this Example demonstrates that the variability in IL-6 levels was profound even in the most critical patients. This might explain why therapeutic approaches targeting the IL-6 receptor have had mixed success along with toxicity in patients who already have multi-organ system failure. Conversely, profoundly increased CCL5/RANTES levels in plasma, as demonstrated herein, may account for liver, renal toxicity but more importantly the mass migration and exhaustion of T-cells and macrophages in the lungs. Treatment with leronlimab in a little as 3 days post-therapy begins to restore T-cell level and correct the gross alteration of CD4/CD8 ratio. CCR5 blockade can prevent the migration of FoxP3+ t-regulatory cells (Tregs) into the tumor microenvironment. Similarly, CCR5 blockade may repolarize macrophages from pro-inflammatory cytokine including IL-6 producing M2 macrophages to anti-tumor M1 macrophages. The results disclosed herein suggest that a similar mechanism of action is effective against COVID-19.

T-cell exhaustion was first described in mice during chronic lymphocyte choriomeningitis virus (LCMV) infection and more recently in infections such as HCV and HBV as well as cancer. T-cell exhaustion though common in chronic infections has been demonstrated to occur as a function of antigen (viral) load (richter) and can occur in as little as 2 weeks. These data are consistent with the data presented in this report demonstrating persistent viral load over the first 7 days of treatment. Further evidence of T-cell exhaustion in the present study is the increased expression of T-cell exhaustion markers PD-1 and LAG3 on both CD4 and CD8 T-cells. Following 7 days of leronlimab, the expression of PD-I and LAG3 significantly decreases compared to Day 0. Interestingly, correlation of PD-1 and LAG3 with liver function in these patients as reflected by decreased in liver transaminases.

CCL5/RANTES has been demonstrated to cause acute renal failure and liver toxicity, both common findings in COVID-19 infection. All 10 of the patients in the current study has some degree of renal failure before administration of leronlimab.

In summary, six out of 10 critically ill patients with COVID-19 survived by Day 14 with 4 patients extubated and released. This compared to a study of critically ill patients in Wuhan, China, where 31 out of 32 patients died. Further, all patients exhibited immune restoration including T-cell numbers and improvement in exhaustion markers. As important, all patients showed significantly decreased IL-6 by Day 7 while CCL5/RANTES levels remained high yet blocked by close to 100% CCR5 receptor occupancy at Day 7. Patients where Day 14 data was available exhibited initiation of a drop in the level of CCL5/RANTES.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method of treating a subject for COVID-19, the method comprising:
    administering to the subject a CCR5/CCL5 interaction inhibitor to treat the subject for COVID-19,
    wherein the CCR5/CCL5 interaction inhibitor is Maraviroc.
2. The method according to claim 1, wherein the COVID-19 is mild, moderate, severe or critical.
3. The method according to claim 1, wherein the COVID-19 is severe or critical.

* * * * *